United States Patent
Nacey

(10) Patent No.: US 7,870,008 B2
(45) Date of Patent: Jan. 11, 2011

(54) SYSTEM FOR COMMERCIAL FOOD MANAGEMENT

(75) Inventor: Gene E. Nacey, Leechburg, PA (US)

(73) Assignee: Tele-Tracking Technologies, Inc., Pittsburgh, PA (US)

( * ) Notice: Subject to any disclaimer, the term of this patent is extended or adjusted under 35 U.S.C. 154(b) by 1211 days.

(21) Appl. No.: 09/808,423

(22) Filed: Mar. 14, 2001

(65) Prior Publication Data

US 2002/0042745 A1 Apr. 11, 2002

Related U.S. Application Data

(60) Provisional application No. 60/189,128, filed on Mar. 14, 2000.

(51) Int. Cl.
*G06F 19/00* (2006.01)

(52) U.S. Cl. .............................................. 705/3; 705/2

(58) Field of Classification Search ................ 705/2, 705/10, 16, 15, 26, 3, 1, 28, 4, 27, 7; 707/3, 707/104.1, 204; 434/127, 400; 600/300, 600/301, 547, 586; 706/217; 426/106; 424/9.1, 424/489, 439, 490, 638; 235/462.45, 375; 709/217; 340/573.1; 379/93.12
See application file for complete search history.

(56) References Cited

U.S. PATENT DOCUMENTS

| | | | | |
|---|---|---|---|---|
| 5,412,560 A * | 5/1995 | Dennison | .................. | 600/300 |
| 5,454,721 A * | 10/1995 | Kuch | ....................... | 434/127 |
| 5,704,350 A * | 1/1998 | Williams, III | ............... | 600/300 |
| 5,819,735 A * | 10/1998 | Mansfield et al. | .......... | 600/300 |
| 5,890,128 A * | 3/1999 | Diaz et al. | .................... | 705/2 |
| 5,954,640 A * | 9/1999 | Szabo | ......................... | 600/300 |
| 6,168,563 B1 * | 1/2001 | Brown | ....................... | 600/301 |
| 6,246,998 B1 * | 6/2001 | Matsumori | .................. | 705/27 |
| 6,290,646 B1 * | 9/2001 | Cosentino et al. | .......... | 600/300 |
| 6,356,940 B1 * | 3/2002 | Short | ......................... | 709/217 |
| 6,370,513 B1 * | 4/2002 | Kolawa et al. | ............... | 705/10 |
| 6,426,077 B1 * | 7/2002 | Grace et al. | ................ | 424/400 |
| 6,458,080 B1 * | 10/2002 | Brown et al. | ................ | 600/300 |
| 6,553,386 B1 * | 4/2003 | Alabaster | ................. | 707/104.1 |
| 6,872,077 B2 * | 3/2005 | Yeager | ....................... | 434/127 |
| 6,980,999 B1 * | 12/2005 | Grana | ..................... | 707/104.1 |
| 2001/0025279 A1 * | 9/2001 | Krulak et al. | .................. | 707/3 |
| 2002/0004749 A1 * | 1/2002 | Froseth et al. | ................ | 705/16 |
| 2002/0015723 A1 * | 2/2002 | Koenig | ....................... | 424/439 |

(Continued)

OTHER PUBLICATIONS

Petot, et al., An artificial intelligence system for computer-assisted menu planning. American Dietetic Association. Journal of the American Dietetic Association. Chicago: Sep. 1998.vol. 98, Iss. 9; p. 1009, 6 pgs.*

(Continued)

*Primary Examiner*—Gerald J. O'Connor
*Assistant Examiner*—Natalie A Pass
(74) *Attorney, Agent, or Firm*—Metz Lewis Brodman Must O'Keefe LLC; Barry I. Friedman

(57) ABSTRACT

A system and method for commercial food management. Nutritional information for identified food items is stored on a central server, along with recipes using the food items. Each recipe is assigned a diet type, and using the nutritional information, menus for a requested diet type are prepared.

37 Claims, 3 Drawing Sheets

U.S. PATENT DOCUMENTS

2002/0046060 A1* 4/2002 Hoskyns et al. .................. 705/2
2003/0091964 A1* 5/2003 Yeager ........................ 434/127
2004/0091843 A1* 5/2004 Albro et al. .................. 434/127

OTHER PUBLICATIONS

Marling, et al., "A CBR/RBR Hybrid for Designing Nutritional Menus," AAAI Technical Report SS-98-04, AAAI Spring Symposium on Multimodal Reasoning, Stanford University, Mar. 1998, pp. 152-156. [Retrieved from Internet Aug. 28, 2009]. URL: <http://www.aaai.org/Papers/Symposia/Spring/19 98/SS-98-04/SS98-04-028.pdf>.*

Marling, et al., Integrating CBR and RBR for Nutritional Menu Design,). In Case-Based Reasoning Integrations: Papers from the 1998 Workshop, 102-107. Menlo Park, Calif.: AAAI Press. [Retrieved from Internet Aug. 28, 2009]. URL: <http://www.aaai.org/Papers/Workshops/1998/WS- 98-15/WS98-15-019.pdf>.*

Nutrition Software: 101 Questions to Ask Before you Buy. Today's Dietitian: The Magazine for Nutrition Professionals. Feb. 2000 issue, vol. 2 No. 2. [Retrieved from Internet Aug. 28, 2009]. URL: <http://www.dietsoftware.com/docs/101.pdf>.*

Marling, et al., "Integrating Case-Based and Rule-Based Reasoning to Meet Multiple Design Constraints" Computational Intelligence, 15(3):308-332, 1999. [Retrieved from Internet Aug. 28, 2009]. URL: <http://oucsace.cs.ohiou.edu/~marling/cbr_rbr.pdf>.*

* cited by examiner

SYSTEM FOR COMMERCIAL FOOD MANAGEMENT

RELATED APPLICATIONS

This application claims priority from pending U.S. Provisional Application Ser. No. 60/189,128 filed on Mar. 14, 2000, which is hereby incorporated by reference.

FIELD OF THE INVENTION

The present invention relates generally to a commercial food management system, and more particularly to a system and method for managing food service in a hospital.

BACKGROUND OF THE INVENTION

Commercial food operations, including those in health care facilities, have long implemented on site food service automation systems to help run the operations. One such commercially available automation system is the Hospitality Suite® software package from Computrition, Inc., Chatsworth, Calif. Typically) existing food service automation systems automate the existing functionality of the sole facility or organization in which they are placed. As such, there is a high degree of customization involved and the food service automation system is site or organization specific.

For a commercial food operation in any facility, the installation of a food service automation system is disruptive, both operationally and economically. For traditional automation solutions, the average implementation time is about nine months to one year, with larger facilities easily taking eighteen months or more. A factor in the length of time needed for implementation, particularly in a health care facility, is the need to build food, diet type, nutrition and menu databases specific to the site (or organization) so that specific dietary requirements and restrictions as prescribed by the physician community may be met while providing patients with substantial variety and flexibility in their meals. The cost of these systems, typically $60,000 to $500,000, has created a market that is only suited for medium to large facilities. Because of the combination of the entry costs, both economic and operational, commercial food service automation systems typically focus on medium to large facilities, which are more likely to have the resources to absorb these costs.

There are, however, approximately 4,330 hospitals under 200 beds in the United States. This represents seventy-one percent of all acute care facilities in the nation. In addition, there are approximately 16,700 long term care facilities in the United States of which approximately 15,400 are under 200 beds. Many times these small facilities are located in rural areas and do not have either the professional or financial resources of the larger facilities. Small facilities having commercial food operation outside of the health care field also face similar resource constraints.

Even though smaller facilities could gain the most from automation, they face the greatest barriers to the automation of their commercial food operations. A need has thus been recognized in conjunction with facilitating the automation of commercial food operations of smaller facilities, and in particular, smaller health care facilities.

SUMMARY OF THE INVENTION

The present invention, in accordance with at least one presently preferred embodiment, utilizes the capabilities of a global computer network to make automation of commercial food operations viable for smaller facilities. Specifically, information needed to prepare nutritionally appropriate menus is preferably located remotely from a user, such as a health care facility.

In one aspect, the present invention broadly contemplates a system for facilitating commercial food management, the system comprising means for recognizing an authorized user accessing the system remotely; means for providing at least one suggested menu which meets predetermined nutritional criteria; and means for providing nutritional information relating to said at least one suggested menu.

In another aspect, the present invention provides a system for facilitating commercial food management, the system comprising a memory device for storing information relating to nutritional values associated with food; a processor in communication with said memory device, said processor being adapted to: create at least one suggested menu which meets predetermined nutritional criteria; output said at least one suggested menu to at least one authorized user located remotely from said memory device; and make available to the at least one authorized user the nutritional information associated with said at least one menu.

In another aspect, the present invention provides a method for facilitating commercial food management, the method comprising the steps of authorizing at least one remote recipient to receive information; creating at least one suggested menu which meets predetermined nutritional criteria; providing for computer-based viewing of the at least one suggested menu; and making available to the at least one authorized recipient nutritional information associated with the at least one menu.

In an additional aspect, the present invention provides a program storage device readable by machine for tangibly embodying a program of instructions executable by said machine to perform a method of commercial food management, said method comprising the steps of authorizing at least one remote recipient to receive information; creating at least one suggested menu which meets predetermined nutritional criteria; providing for computer-based viewing of the at least one suggested menu; and making available to the at least one authorized recipient nutritional information associated with the at least one menu.

For a better understanding of the present invention, together with other and further features and advantages thereof, reference is made to the following description, taken in conjunction with the accompanying drawings, and the scope of the invention will be pointed out in the appended claims.

DETAILED DESCRIPTION OF THE PREFERRED EMBODIMENTS

Figure 1:
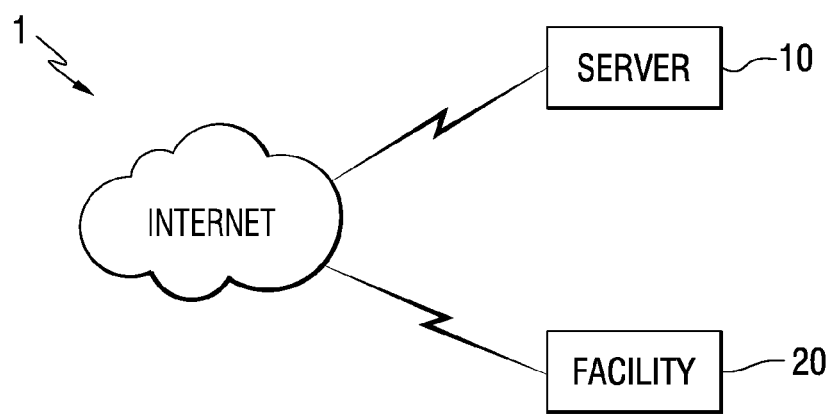
FIG. 1 is an overall system block diagram of a presently preferred embodiment of the present invention.

FIG. 1 is an overall system block diagram of a presently preferred embodiment of the present invention. In this embodiment, a central server 10 is linked up to at least one remote computer 20 located in a health care facility. Only one remote computer is depicted in FIG. 1, but any number of remote computers may be used. Furthermore, as discussed below, the remote computers need not be located in the same facility. The link 1 between the central server 10 and the remote computer 20 does not have to be a physical link—it can, for example, be a link via a global computer network as described below, or any other link, including a virtual private network.

The system depicted in FIG. 1 is preferably implemented using existing general purpose computers. Changes to the existing computers to incorporate the present invention may be accomplished in various ways, such as by reprogramming an existing file server or additional file servers. Preferably, the link 1 is a global communications network such as the Internet. Use of a global communications network reduces the cost of implementing the present invention since a private communications network need not be provided, while increasing the geographical range of potential system users. Alternatively, link 1 can be a private communications network, or other appropriate means, such as a direct dial modem connection. The link may also be a secure link, secured for example, through cryptography. The central server 10 is preferably accessed using a standard software browser, such as Netscape Navigator or Microsoft Internet Explorer.

Figure 2:
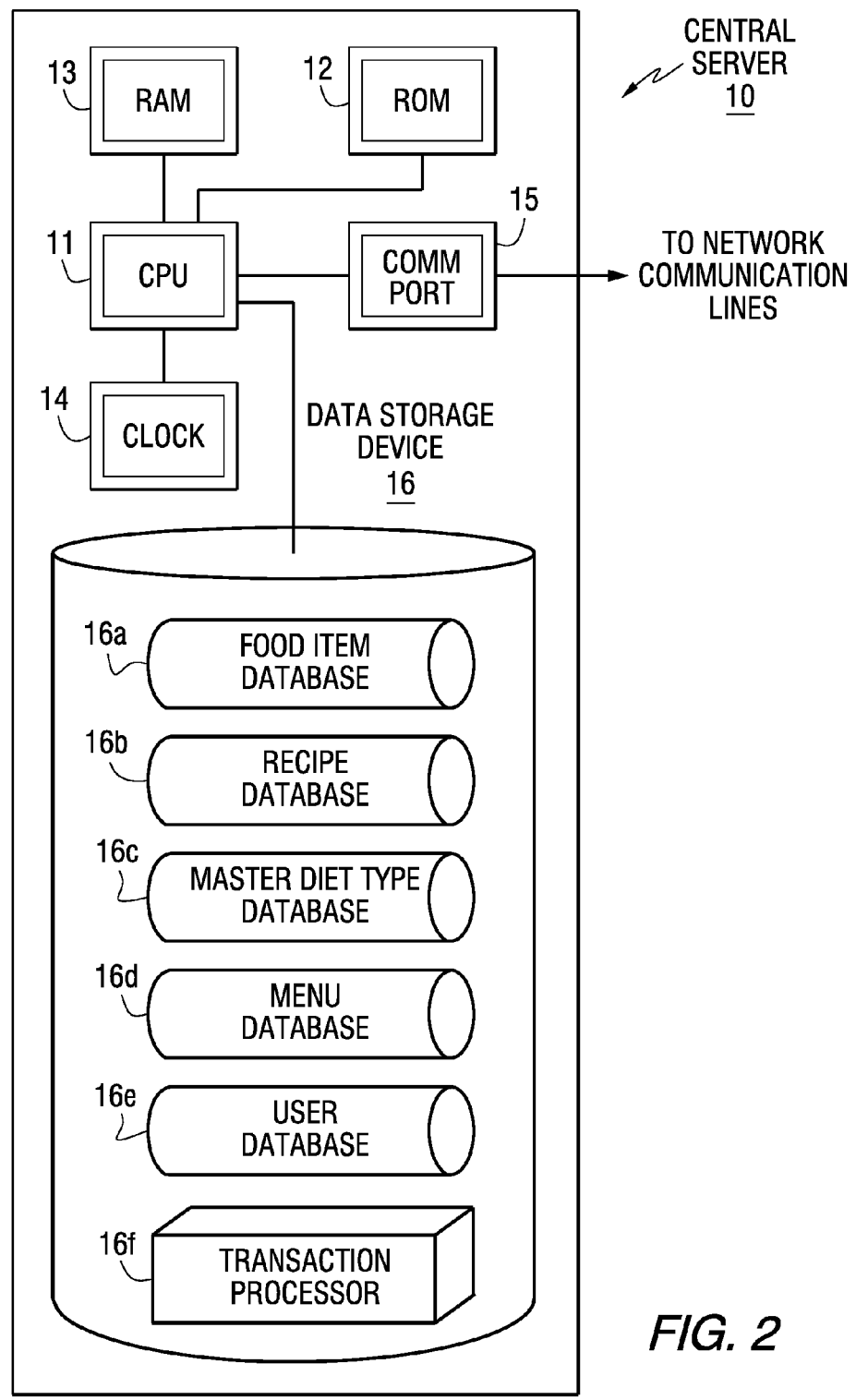
FIG. 2 is an overall system block diagram of a central server in accordance with an embodiment of the present invention.

FIG. 2 is a block diagram of a preferred central server 10. The central server includes a CPU 11 which performs the processing functions of the controller. It also includes a read only memory 12 (ROM) and a random access memory 13 (RAM). The ROM 12 is used to store at least some of the program instructions that are to be executed by the CPU 11, such as portions of the operating system or BIOS, and the RAM 13 is used for temporary storage of data. A clock circuit 14 provides a clock signal which is required by the CPU. The use of a CPU in conjunction with ROM, RAM, and a clock circuit is well known to those skilled in the art of CPU based electronic circuit design. The central server 110 also includes a communications port 15 which enables the CPU 11 to communicate with devices external to the central server 10. In particular, the communications port 15 facilitates communication between the network communication lines and the CPU 11, so that information arriving from the network communication lines can be processed by the CPU 11, and the CPU 11 can send information to remote locations. While the illustrated embodiment uses a hard-wired connection to devices outside the central server 10, it should be understood that other methods of communicating with external devices may be used. These other methods include a modem, radio communications, optical communications, and the like.

As shown in FIG. 2, the CPU 11 can also store information to, and read information from, data storage device 16. This data storage device 16 includes food item database 16a, recipe database 16b, master diet type database 16c, menu database 16d, and user database 16e, which are described below. Additional databases may also be included. In addition, it includes transaction processor instructions 16f, which can be read by and executed by the CPU 11, thereby enabling the CPU 11 to process transactions. While FIG. 2 depicts separate food, recipe, master diet type, menu, and user databases, a single database which incorporates all of those functions can also be used.

Figure 3:
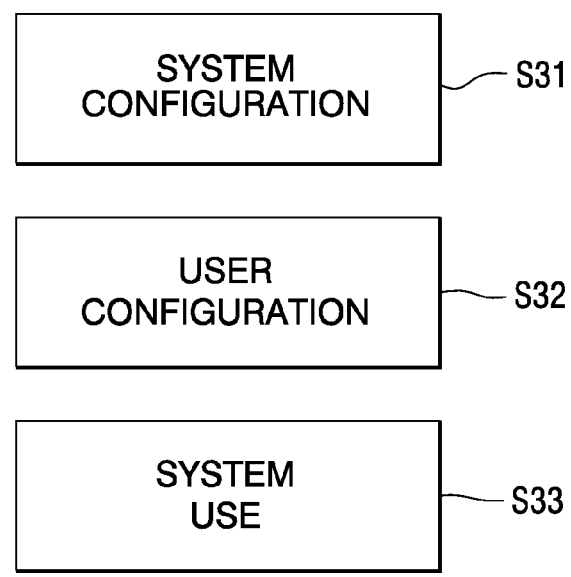
FIG. 3 is an overall block diagram of the method of the present invention in accordance with an embodiment of the present invention.

FIG. 3 is a flow chart of the overall process of one embodiment of the present invention. The process starts with the system proprietor configuring the system for use at Step S31, which primarily consists of initializing the food item database 16a, recipe database 16b, master diet type database 16c, and menu database 16d.

There are certain required items, such as nutrients, vitamins and minerals, which must be supplied to the body by food. These essentials are included in every adequate diet and must also be supplied by any therapeutic diet on which a person is expected to live for any extended period of time. While emergencies arise which require the use of temporary diets which are obviously inadequate from the standpoint of good nutrition, as soon as possible the temporary diet should be exchanged for one which supplies the body's needs. In therapeutic diets, interest may be directed to some specific nutrient, as in a diabetic diet where attention is focused on the metabolism of glucose, but the diet will not be permanently successful if any of the essential nutrients are not provided. Against this backdrop, health care facilities have a number of different diet types. Typically, each facility or organization has developed its own diet types. Examples of different diet types include clear liquid, full liquid, soft, bland, regular, diabetic, calorie specific diets (1000, 1200, 1500, 1800, etc.; regular or diabetic); low sodium; and no sodium or sodium restricted.

In a health care facility, all food items (or ingredients) must have known nutritional values in order for clinical dietitians to ensure that a patient receives the essential nutrients contained within the diet type selected by the patient's physician. Thus, the food item database 16a preferably contains nutritional data on each food item used in a recipe contained within the recipe database. This nutritional data may either be obtained from the food composition data made available by the U.S. Department of Agriculture (see [http://]www.nal.usda.gov/fnic/foodcomp/) or directly from the manufacturer.

Recipe database 16b preferably contains recipes that food service professionals can use, modify or add to. These recipes are preferably categorized for each region of the country where there are noticeable differences in food tastes. Preferably the nutritional value and readings of all completed recipes are verified. Furthermore, it is preferably possible to search the recipes by food/ingredients.

Master diet type database 16c preferably contains a set of diet types defined by the system proprietor. This creates a standard set of diet types, eliminating variances in diet types among differing facilities or organizations. As part of the initialization process, all food items and recipes are qualified. This is accomplished through evaluating the appropriate items ranging from the nutritional content of each food to the diabetic exchange rates they represent. It is contemplated that as many as 200 to 300 diet types can be established, although a lesser or greater number may also be established.

In the traditional food commercial food service operation that adopts automation technology, the menus are one of the most "individual" or "variable" of all facets. A typical menu cycle changes every two weeks. Each day contains three meals, and each meal has 5 to 7 courses, and each course can contain 4 to 6 selections. Since each of the aforementioned must be shaped for every diet type that is established, the number of different possibilities is staggering. Consequently, this phase of account preparation can also consume enormous amounts of time from limited food service staff personnel. Menu database 16d preferably contains a large library of complete menu sets. Food service managers are preferably able to choose a set of menus from the library of complete menu sets. Alternatively, a set of menus may be suggested based upon the food products currently in stock at the facility (or organization) using the present invention. Menus may also be suggested based upon a patient's preference, including the patient's likes, dislikes, and religious beliefs.

User database 16e preferably contains information on the registered users of the present invention. Such information may include identifying information, along with historical information on the user's use of the present invention.

At Step S32, an authorized user configures the system for use within the user's facility or organization. One of the main tasks during configuration is to select the master diet types to be used within the facility (or organization). Preferably, user configuration is limited to appropriate personnel within the facility or organization.

At Step S33, the system is used by an authorized user. Use typically involves menu selection based upon any number of criteria. Various food attributes of meals and menus have preferably been assigned as part of the initialization of menu database 16d, and these attributes are preferably used in the menu selection.

In another preferred embodiment, the system of the present invention includes a database which permits tracking of the inventory of food items at a health care facility. The ability to manage inventory is a critical component of any food service operation. In fact, it may be more critical than any commercial enterprise, in that most food products have limited shelf life and potential loss from a lack of control can be a very serious problem. Unfortunately, the act of taking inventory in a commercial food operation can be quite time consuming and also inaccurate if it is done on a manual basis. In addition, as shown in FIG. 4, the tracking of inventory creates an opportunity for vendor/food supplier involvement as well— allowing on-line ordering and automatic updating of inventory.

Figure 4:
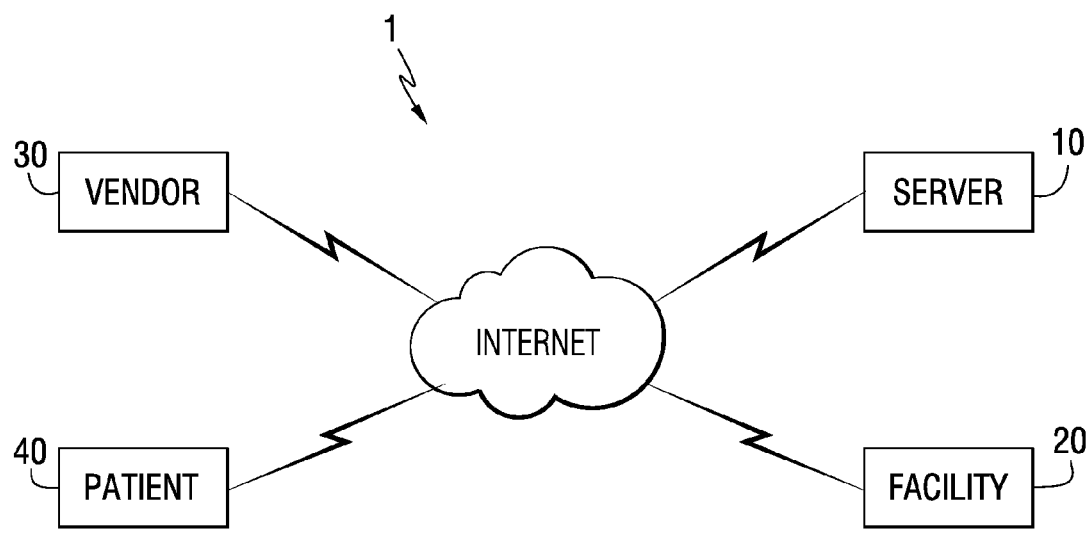
FIG. 4 is an overall system block diagram of another embodiment of the present invention.

FIG. 4 is an overall system block diagram of another preferred embodiment of the present invention. Like reference numerals are used to denote like components. As before, a central server 10 is linked up to at least one remote computer 20 located in a health care facility. Additionally, remote computers at vendor 30 and patient 40 are linked to the central server 10. In actuality, either one of these additional computers may be linked.

When a remote computer at vendor 30 is linked to the central server 10, a health care facility may order its food supplies through the system of the present invention. E-Commerce has become a "main stream" reality in the 90s. This form of doing business presents many advantages from traditional shopping for both the buyer and the seller. The seller can save the cost of sales staff, and related support personnel, while the buyer can generally do better comparative pricing when most (if not all) sellers have posted prices online. Preferably, more than one food distributor (supplier) is included in the online ordering capability of the present invention. Furthermore, the information regarding a transaction is preferably formatted in a standard manner thereby permitting managers to make objective decisions about their food and sundry supply needs.

When a remote computer at patient 40 is linked to the central server 10, additional information may be conveyed within the system of the present invention. In this embodiment, "patient" is used to identify an additional remote computer. Such additional remote computer may or may not be located within a patient room at a health care facility. The use of an additional remote computer permits a degree of interactivity between a user of the system, either at the patient level or manager level, and the system proprietor. For example, questions one may have may be submitted electronically to the system provider. Preferably, the system provider maintains staff across two shifts that can answer email and "real time" questions interactively. Such questions may include nutritional questions.

In another preferred embodiment, additional databases are maintained permitting new users to chat with experienced users. Such users would include both managers, chefs, and nutritionists. Through the use of this database, users can share their experiences with various foods, recipes and menus, and even the entire system, thus helping them to make better use of the technology and potentially providing feedback to the system proprietor for future enhancements.

In another preferred embodiment, a search engine is provided to permit searches of the databases maintained within the system of the present invention. Of particular interest in research is searching for information relating to food items and nutritional components.

In recapitulation, the present invention, in accordance with at least one presently preferred embodiment, provides a system and method for managing commercial food service operations. As such, it is to be understood that the present invention, in accordance with at least one presently preferred embodiment, may be utilized in environments other than hospitals, such as long term care facilities, hospices, or any other environment in which there is a commercial food service operation.

It is to be understood that the present invention, in accordance with at least one presently preferred embodiment, includes recognizing an authorized user accessing the system remotely, providing at least one suggested menu which meets predetermined nutritional criteria, and providing nutritional information relating to said at least one suggested menu. Together, these may be implemented on at least one general-purpose computer running suitable software programs. These may also be implemented on at least one Integrated Circuit or part of at least one Integrated Circuit. Thus, it is to be understood that the invention may be implemented in hardware, software, or a combination of both.

If not otherwise stated herein, it is to be assumed that all patents, patent applications, patent publications and other publications mentioned and cited herein are hereby fully incorporated by reference herein as if set forth in their entirety herein.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for facilitating food service management in a health care facility, said method comprising the steps of:

establishing a standard set of therapeutic diet types contained in a master diet type database stored in the memory of a computer-based system;

storing a plurality of food recipes in said memory within a recipe database;

obtaining nutritional data on each food item used in said plurality of recipes and storing said data in said memory within a food item database;

evaluating the nutritional content of each food item, wherein said evaluating is performed by a computer processor;

establishing and storing preselected nutritional criteria in said memory;

verifying a nutritional value of each of said plurality of recipes in said recipe database, wherein said verifying is performed by said processor;

assigning, with said processor, various food attributes to said recipes based upon said verified nutritional values in said memory;

shaping menu sets of said recipes for each of said established therapeutic diet types in a menu database in said memory based upon said assigned food attributes, wherein said shaping menus sets is performed by said processor;

providing a remote electronic data link to food service professionals associated with said healthcare facility to access said data;

collecting information from said food service professionals and storing in said memory;

creating menu sets in accordance with said preselected nutritional criteria to said food service professionals, wherein said creating menu sets is performed by said processor;

providing nutritional information associated with said menu sets electronically available to said food service professionals; and tracking an inventory of food items at said health care facility in said memory.

2. The method of claim 1, further comprising the step of categorizing said plurality of recipes according to geographic regions having noticeable differences in food tastes, wherein said categorizing is performed by said processor.

3. The method of claim 1, further comprising the step of eliminating variances in said therapeutic diet types among differing health care facilities, wherein said eliminating is performed by said processor.

4. The method of claim 1, further comprising the step of evaluating diabetic exchange rates of each food item, wherein said evaluating is performed by said processor.

5. The method of claim 4, wherein said verification of nutritional value of each of said plurality of recipes is based upon said evaluation of nutritional content and said evaluation of diabetic exchange rates of each food item.

6. The method of claim 1, further comprising the step of forming a large library of menu sets in said menu database, wherein said forming a large library of menu sets is performed by said processor.

7. The method of claim 6, further comprising the step of allowing said food service professionals to choose a set of menus from said library.

8. The method of claim 1, further comprising the step of suggesting menu sets to said food service professionals based upon said inventory of food items at said healthcare facility.

9. The method of claim 1, further comprising the step of suggesting menu sets to said food service professionals based upon an individual patient's preference.

10. The method of claim 9, wherein said patient's preference is based upon said patient's particular food tastes.

11. The method of claim 9, wherein said patient's preference is based upon said patient's religious beliefs.

12. The method of claim 1, further comprising the step of storing said information collected from said food service professionals in said system in a user database in said memory.

13. The method of claim 12, wherein said stored information in said user database includes identifying information.

14. The method of claim 12, wherein said stored information in said user database includes historical information on prior use of said system by said food service professionals.

15. The method of claim 1, further comprising the step of limiting access to said system to food service professionals associated with a healthcare facility.

16. The method of claim 1, further comprising the step of authorizing at least one food service professional associated with a healthcare facility to receive information.

17. The method of claim 1, further comprising the step of allowing said food service professionals to place food item orders via said system.

18. The method of claim 17, further comprising the step of automatically updating said inventory to reflect said orders, wherein said updating is performed by said processor.

19. The method of claim 17, wherein said food service professionals can place food item orders with a plurality of food item distributors.

20. The method of claim 19, further comprising the step of providing a standard format for order transactions such that said food service professionals can make objective decisions about placing said orders.

21. The method of claim 1, further comprising the step of providing said food service professionals the ability to interact with a system proprietor.

22. The method of claim 1, further comprising the step of providing said food service professionals the ability to interact with other food service professionals associated with other healthcare facilities.

23. The method of claim 1, further comprising the step of providing a search engine such that said food service professionals can search said databases.

24. A system for facilitating food service management in a healthcare facility, said system comprising:
 a data storage device comprising:
  a master diet type database containing a standard set of therapeutic diet types;
  a recipe database containing a plurality of food recipes;
  a food item database containing nutritional data on each food item used in said plurality of recipes; and
  a menu database containing menu sets shaped for each of said therapeutic diet types;
 a computer-implemented arrangement adapted to perform a function, the function comprising:
  obtaining said nutritional data;
  evaluating a nutritional content of each food item;
  verifying a nutritional value of each of said plurality of recipes m said recipe database;
  establishing preselected nutritional criteria;
  assigning various food attributes to said recipes based upon said verified nutritional values;
  shaping said menu sets based upon said assigned food attributes of said recipes;
  collecting information from food service professionals;
  suggesting menu sets in accordance with said preselected nutritional criteria to said food service professionals;
  making nutritional information associated with said menu sets available to said food service professionals; and
  tracking an inventory of food items at said healthcare facility, and;
 a remote electronic data input and output link, wherein food service professionals associated with said healthcare facility may access the system.

25. The system of claim 24, further comprising a computer-implemented arrangement adapted to perform a function, the function comprising categorizing said plurality of recipes according to geographic regions having noticeable differences in food tastes.

26. The system of claim 24, wherein said menu database contains a large library of completed menu sets.

27. The system of claim 26, further comprising a computer-implemented arrangement adapted to perform a function, the function comprising allowing said food service professionals to choose a set of menus from said library.

28. The system of claim 24, further comprising a computer-implemented arrangement adapted to perform a function, the function comprising suggesting menu sets to said food service professionals based upon said inventory of food items at said healthcare facility.

29. The system of claim 24, further comprising a computer-implemented arrangement adapted to perform a function, the function comprising suggesting menu sets to said food service professionals based upon an individual patient's preference.

30. The system of claim 24, wherein said data storage device further comprises a user database containing information collected from said food service professionals.

31. The system of claim 24, wherein access to the system is limited to food service professionals associated with a healthcare facility.

32. The system of claim 24, further comprising a computer-implemented arrangement adapted to perform a function, the function comprising authorizing at least one food service professional associated with a healthcare facility to receive information.

33. The system of claim 24, further comprising a computer-implemented arrangement adapted to perform a function, the function comprising processing food order transactions placed in the system by said food service professionals.

34. The system of claim 33, further comprising a computer-implemented arrangement adapted to perform a function, the function comprising automatically updating said inventory to reflect said food order transactions.

35. The system of claim 33, wherein said food service professionals can place orders with a plurality of food item distributors.

36. The system of claim 24, wherein said food service professionals are able to interact with a system proprietor or with other food service professionals associated with other healthcare facilities.

37. The system of claim 24, further comprising a search engine adapted to allow said food service professionals to search said databases.

* * * * *

UNITED STATES PATENT AND TRADEMARK OFFICE
CERTIFICATE OF CORRECTION

PATENT NO.       : 7,870,008 B2
APPLICATION NO.  : 09/808423
DATED            : January 11, 2011
INVENTOR(S)      : Gene E. Nacey It is certified that error appears in the above-identified patent and that said Letters Patent is hereby corrected as shown below:

Column 1, line 23, delete "Typically)" and insert -- Typically, --.

Column 8, line 45, "m" should be -- in --.

Signed and Sealed this

Nineteenth Day of April, 2011

David J. Kappos
*Director of the United States Patent and Trademark Office*